United States Patent
Rasor et al.

(10) Patent No.: US 8,398,580 B2
(45) Date of Patent: *Mar. 19, 2013

(54) METHODS AND APPARATUS FOR TREATING RHINITIS

(75) Inventors: Julia S. Rasor, Los Gatos, CA (US); Ned S. Rasor, Cupertino, CA (US); Gerard F. Pereira, San Mateo, CA (US)

(73) Assignee: Capnia, Inc., Palo Alto, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 12/650,341

(22) Filed: Dec. 30, 2009

(65) Prior Publication Data

US 2010/0104665 A1    Apr. 29, 2010

Related U.S. Application Data

(63) Continuation of application No. 11/459,798, filed on Jul. 25, 2006, now abandoned, which is a continuation-in-part of application No. 11/192,852, filed on Jul. 29, 2005, now abandoned, which is a (Continued)

(51) Int. Cl.
*A61M 37/00* (2006.01)

(52) U.S. Cl. ............... 604/24; 604/23; 604/26

(58) Field of Classification Search ............ 604/23, 604/24, 26, 56; 128/203.12
See application file for complete search history.

(56) References Cited

U.S. PATENT DOCUMENTS

| | | |
|---|---|---|
| 1,288,850 A | 12/1918 | Easly |
| 1,449,047 A | 3/1923 | Johnson |
| 1,742,605 A | 1/1930 | Lemoine |
| 2,574,028 A | 11/1951 | Fields et al. |
| 2,585,254 A | 2/1952 | Kochner |
| 2,651,303 A | 9/1953 | Johnson et al. |
| 2,860,634 A | 11/1958 | Duncan et al. |
| 2,920,623 A | 1/1960 | Holt |
| 3,127,058 A | 3/1964 | Johnston |
| 3,425,414 A | 2/1969 | Roche |
| 3,513,843 A | 5/1970 | Exler |
| 3,776,227 A | 12/1973 | Pitesky et al. |
| 3,870,072 A | 3/1975 | Lindermann |
| 3,934,585 A | 1/1976 | Maurice |
| 3,974,830 A * | 8/1976 | LaVerne ............ 128/203.27 |
| 4,067,499 A | 1/1978 | Cohen |

(Continued)

FOREIGN PATENT DOCUMENTS

| | | | |
|---|---|---|---|
| CH | 247 873 A | 3/1947 | |
| DE | 837 158 C | 4/1952 | |

(Continued)

OTHER PUBLICATIONS

Chatkin et al., "Nasal Nitric Oxide is Independent of Nasal Cavity Volume," Am J. Rhinol, 1999, 13(3): 179-84.*

(Continued)

*Primary Examiner* — Bhisma Mehta
*Assistant Examiner* — Larry R Wilson
(74) *Attorney, Agent, or Firm* — Morrison & Foerster LLP

(57) ABSTRACT

Described here are devices and methods for the delivery of treatment agents simultaneously with capnic gases. Specifically, the treatment agents and capnic gases may be delivered to a mucosal membrane at a controlled flow rate to treat rhinitis. Exemplary capnic gases include carbon dioxide, nitric oxide, nitrous oxide, and dilute acid gases.

17 Claims, 7 Drawing Sheets

Related U.S. Application Data continuation-in-part of application No. 09/708,186, filed on Nov. 7, 2000, now Pat. No. 6,959,708.

(60) Provisional application No. 60/185,495, filed on Feb. 28, 2000, provisional application No. 60/164,125, filed on Nov. 8, 1999.

(56) References Cited

U.S. PATENT DOCUMENTS

| | | | |
|---|---|---|---|
| 4,137,914 A | | 2/1979 | Wetterlin |
| 4,175,704 A | | 11/1979 | Cohen |
| 4,188,946 A | | 2/1980 | Watson et al. |
| 4,273,124 A | | 6/1981 | Zimmerman |
| 4,375,812 A | | 3/1983 | Vaseen et al. |
| 4,447,449 A | | 5/1984 | Marshall |
| 4,465,067 A | | 8/1984 | Koch et al. |
| 4,554,916 A | * | 11/1985 | Watt ................ 128/203.12 |
| 4,694,850 A | | 9/1987 | Fumino |
| 4,934,359 A | | 6/1990 | Blaine |
| 5,099,834 A | | 3/1992 | Fishman |
| 5,123,442 A | | 6/1992 | Geuy et al. |
| 5,262,180 A | | 11/1993 | Orlando et al. |
| 5,288,462 A | | 2/1994 | Carter et al. |
| 5,318,015 A | | 6/1994 | Månsson et al. |
| 5,370,862 A | | 12/1994 | Klokker-Bethke et al. |
| 5,431,155 A | | 7/1995 | Marelli |
| 5,485,827 A | | 1/1996 | Zapol et al. |
| 5,490,498 A | | 2/1996 | Faithfull et al. |
| 5,525,130 A | | 6/1996 | Beaudry |
| 5,558,083 A | | 9/1996 | Bathe et al. |
| 5,562,644 A | | 10/1996 | McLeod |
| 5,570,683 A | | 11/1996 | Zapol |
| 5,807,357 A | | 9/1998 | Kang |
| 5,839,433 A | | 11/1998 | Higenbottam |
| 5,848,998 A | | 12/1998 | Marasco, Jr. |
| 5,851,544 A | | 12/1998 | Penska et al. |
| 5,855,907 A | | 1/1999 | Peyman |
| 5,875,776 A | | 3/1999 | Vaghefi |
| 5,891,885 A | | 4/1999 | Caruso |
| 5,908,870 A | | 6/1999 | McLeod |
| 5,918,596 A | * | 7/1999 | Heinonen ............. 128/204.21 |
| 5,938,590 A | | 8/1999 | Elliott |
| 5,941,241 A | | 8/1999 | Weinstein et al. |
| 5,951,538 A | | 9/1999 | Joshi et al. |
| 5,983,891 A | | 11/1999 | Fukunaga |
| 5,993,428 A | | 11/1999 | Hardge |
| 6,001,332 A | | 12/1999 | Garrett |
| 6,113,922 A | | 9/2000 | Swenson et al. |
| 6,125,844 A | * | 10/2000 | Samiotes ............. 128/200.23 |
| 6,258,032 B1 | | 7/2001 | Hammesfahr |
| 6,581,539 B1 | | 6/2003 | Rasor |
| 6,638,236 B2 | | 10/2003 | Thrash et al. |
| 6,652,479 B2 | | 11/2003 | Rasor et al. |
| 6,706,892 B1 | | 3/2004 | Ezrin et al. |
| 6,780,400 B2 | | 8/2004 | Rabinowitz et al. |
| 6,959,708 B1 | | 11/2005 | Rasor et al. |
| 7,017,573 B1 | | 3/2006 | Rasor et al. |
| 7,748,379 B2 | | 7/2010 | Rasor et al. |
| 7,827,986 B2 | | 11/2010 | Rasor et al. |
| 7,836,883 B2 | | 11/2010 | Rasor et al. |
| 7,845,347 B2 | | 12/2010 | Rasor et al. |
| 7,845,348 B2 | | 12/2010 | Rasor et al. |
| 2004/0260253 A1 | | 12/2004 | Rosati |
| 2005/0228337 A1 | | 10/2005 | Rasor et al. |
| 2006/0076011 A1 | | 4/2006 | Rasor et al. |
| 2006/0172017 A1 | | 8/2006 | Rasor et al. |
| 2006/0251542 A1 | | 11/2006 | Sims |
| 2007/0039615 A1 | | 2/2007 | Rasor et al. |
| 2008/0132825 A1 | | 6/2008 | Rasor et al. |
| 2008/0169047 A1 | | 7/2008 | Connolly et al. |
| 2010/0152120 A1 | | 6/2010 | Rasor et al. |
| 2010/0210565 A1 | | 8/2010 | Rasor et al. |
| 2011/0040240 A1 | | 2/2011 | Rasor et al. |
| 2011/0046546 A1 | | 2/2011 | Rasor et al. |

FOREIGN PATENT DOCUMENTS

| | | |
|---|---|---|
| DE | 14 91 660 A1 | 8/1969 |
| DE | 89 06 590 U | 10/1989 |
| DE | 14 91 660 A1 | 12/1994 |
| DE | 43 19 612 A1 | 12/1994 |
| DE | 195 48 652 A1 | 10/1997 |
| EP | 0 198 708 A2 | 10/1986 |
| EP | 0 768 094 A | 4/1997 |
| FR | 2 656 218 A1 | 6/1991 |
| GB | 408856 A | 4/1934 |
| JP | 08-224321 | 9/1996 |
| JP | 09-084876 | 3/1997 |
| WO | WO-91/08793 A1 | 6/1991 |
| WO | WO-93/00951 A1 | 1/1993 |
| WO | WO-95/23596 A1 | 9/1995 |
| WO | WO 97/42992 A1 | 11/1997 |
| WO | WO 99/29249 A1 | 6/1999 |
| WO | WO-00/51672 A1 | 9/2000 |
| WO | WO-00/57851 A2 | 10/2000 |
| WO | WO-00/57851 A3 | 10/2000 |
| WO | WO-01/03645 A2 | 1/2001 |
| WO | WO-01/03645 A3 | 1/2001 |
| WO | WO-01/64280 A1 | 9/2001 |

OTHER PUBLICATIONS

Non-Final Office Action mailed on Mar. 20, 2002, for U.S. Appl. No. 09/708,186, filed Nov. 7, 2000, 6 pages.

Non-Final Office Action mailed on Jun. 13, 2003, for U.S. Appl. No. 09/708,186, filed Nov. 7, 2000, 6 pages.

Non-Final Office Action mailed on Jan. 30, 2004, for U.S. Appl. No. 09/708,186, filed Nov. 7, 2000, 6 pages.

Non-Final Office Action mailed on Nov. 2, 2004, for U.S. Appl. No. 09/708,186, filed Nov. 7, 2000, 8 pages.

Non-Final Office Action mailed Sep. 1, 2010, for U.S. Appl. No. 12/708,407, filed Feb. 18, 2010, 13 pages.

Notice of Allowance mailed on Sep. 29, 2011, for U.S. Appl. No. 12/708,407, filed Feb. 18, 2010, 8 pages.

ABCNEWS.COM. (Jun. 13, 2001). "Can't Stop the Pain: Cluster Headaches Can Make Life Unbearable," located at <www.abcnew.go.com/sections/GMZ/GoodMorningAmerica/GMA010530Headaches_Cluster.Html>, last visited Nov. 7, 2002, 3 pages.

Aizawa, H. et al. (1999). "Role of Nitric Oxide Released from iNANC Neurons in Airway Responsiveness in Cats," *European Respiratory Journal* 13:775-780.

Anonymous. (2001-2002). "Yoga Rx for Headaches," located at <www.yogabasics.com/articles/headaches.html>, last visited Nov. 7, 2002, 2 pages.

Anton, F. et al. (1992). "Psychophysical Examination of Pain Induced by Defined $CO_2$ Pulses Applied to the Nasal Mucosa," *Pain* 49:53-60.

Casale, T.B. et al. (Jan. 2008). "Intranasal Noninhaled Carbon Dioxide for the Symptomatic Treatment of Seasonal Allergic Rhinitis," *J. Allergy Clin. Immunol.* 121(1):105-109.

Cha, E.J. et al. (1987). "Changes in Lung Volume and Breathing Pattern During Exercise and $CO_2$ Inhalation in Humans," *J. Appl. Physiol.* 62(4):1544-1550.

Dexter, S.L. (1981). "Rebreathing Aborts Migraine Attacks," *Br. Med. J.* pp. 312.

Echarri, R.M. et al. (Aug.-Sep. 2000). "Sudden Hearing Loss: Effectiveness of a Therapeutic Protocol," *Acta Otorrinolaringol Esp* 51(6):490-494. (English Abstract).

Faisy, C. et al. (1999). "Utilisation du Mélange Hélium_Oxygène en Pratique Pneumologique," *Rev mal Respir* 16:1063-1073. (French Language).

Fiermonte, G. et al. (1995). "Cerebrovascular $CO_2$ Reactivity in Migraine with Aura and Without Aura, A Transcranial Study," *Acta Neurol. Scand.* 92:166-169.

Fisher, H.K. et al. (1970). "Resistance to Breathing During Exercise-Induced Asthma Attacks," *American Review of Respiratory Disease* 101:855-896.

Fisher, H.K. et al. (1976). "Site of Action of Inhaled 6 Percent Carbon Dioxide in the Lungs of Asthmatic Subjects Before and After Exercise," *American Review of Respiratory Disease* 114:861-870.

Gillman, M.A. et al. (1991). "Placebo and Analgesic Nitrous Oxide for Treatment of the Alcohol Withdrawal State," *British Journal of Psychiatry* 159:672-675.

Glovsky, M.M. (1998). "Upper Airways Involvement in Bronchial Asthma," *Current Opinion in Pulmonary Medicine* 4:54-58.

Goebel, K.M. et al. (Jan. 30, 1982). "Rebreathing Aborts Migraine Attacks," *British Medical Journal* 284:312.

Grönross, M. et al. (1994). "A Selective suppression of Human Pain Sensitivity by Carbon Dioxide: Central Mechanisms Implicated," *European Journal of Applied Physiology* 68:74-79.

Grosser, K. et al. (2000). "Olfactory and Trigeminal Event-Related Potentials in Migraine," *Cephalalgia* 20:621-670.

Grosshans, A. (1987). "$CO_2$-Gasinjection—Indications and Results," *Z Gesamte Inn. Med.* 42(23):667-670. (English Translation).

Groth, S. et al. (Oct. 1984). "Intranasal Fenoterol in Asthmatic Subjects: An Alternative Route of Administration," *Journal of Clinical Immunology*, 74(4)(1):536-539.

Guyton, A.C. et al. (1996). "The Textbook of Medical Physiology" W.B. Saunders Company: Philadelphia, Pennsylvania, pp. 101. 203-204, 206-207, 454, 487, 515, 520-523, 527-530, 541-544, 572-573, 619-619, 694.

Harrowes, W.M.C. et al, (1958). "Fractional Administration of Carbon Dioxide in the Treatment of Neuroses," in *Carbon Dioxide Therapy a Neurophysiological Treatment of Nervous Disorders. 2nd Edition*, L.J. Meduna ed., Bannerstone House: Springfield, IL. pp. 294-305.

Hollman, G. et al. (1998). "Helium-Oxygen Improves Clinical Asthma Scores in Children with Acute Bronchiolitis," *Crit. Care Med.* 26(10):1731-1736.

Hummel, T. et al. (1997). "Comparison of the Antinociception Produced by Two Oral Formulations of Ibuprofen: Ibuprofen Effervescent vs Ibuprofin Tablets," *Eur J Clin Pharmacol* 52:107-114.

Hurst, A.F. (Feb. 1931). "The Use of Carbon Dioxide in the Treatment of Vasomotor Rhinitis, Hay Fever, and Asthma," *Proc. R. Soc. Med.* pp. 441-442.

Jolliet, P. et al. (1999). "Beneficial Effects of Helium-Oxygen Versus Air:Oxygen Noninvasive Pressure Support in Patients with Decompensated Chronic Obstruction Pulmonary Disease," *Crit. Care Med.* 27(11):2422-2429. (missing last page).

Josefowicz, R.F. (Aug. 1989). "Neurologic Manifestations of Pulmonary Disease," *Neurologic Clinics* 7(3):605-616.

La Verne "Rapid Coma Technique of Carbon Dioxide Therapy," in *Carbon Dioxide Therapy a Neurophysiological Treatment of Nervous Disorders. 2nd Edition*. L.J. Meduna ed., Bannerstone House: Springfield, IL. pp. 269-293, Feb. 1958.

La Verne, A.A. (May 1953). "Rapid Coma Technique of Carbon Dioxide Therapy," *Diseases of the Nervous System* 14(5):141-144.

Leake, C.D. (1925). "The Historical Development of Surgical Anesthesia," *The Scientific Monthly* 20:304-320.

Leake, C.D. et al. (Jul. 1929). "The Stimulating Effect of Carbon Dioxid Inhalations in Dementia Praecox Catatonia," *Calif West Med.* 31(1):20-23.

Lipkin, A.F. et al. (Mar. 1987). "Migraine and Sudden Sensorineural Hearing Loss," *Arch Otolarynhol Head Neck Surg* 113: 325-26.

Loevenhart, A.S et al. (Mar. 16, 1929). "Cerebral Stimulation," *JAMA* 92(11):880-883.

Loh, E. et al. (1999). "Cardiovascular Effects of Inhaled Nitric Oxide in a Canine Model of Cardiomyopathy," *Ann Thorac Surg* 67(5): 1380-1385.

Lorente De Nó, R. (1946) "Carbon Dioxide and Nerve Function," Chapter III in *A Study of Nerve Physiology, Studies of the Rockefeller Institute for Medical Research*, 131:149-194.

Macrae, L.D. (1958). "Carbon Dioxide in Pediatrics," in *Carbon Dioxide Therapy a Neurophysiological Treatment of Nervous Disorders. 2nd Edition*, L.J. Meduna ed., Bannerstone House: Springfield, IL. pp. 146-164.

Marcussen, R.M. et al. (1950). "Studies on Headache," vol. 63 in *Archives of Neurology and Psychiatry*, Putnam, T.J. ed et al. American Medical Association: Chicago, IL, pp. 43-51.

Meduna, L.J. (Feb. 1947). "Pharmaco-Dynamic Treatment of Pyschoneuroses (A Preliminary Report)," *Diseases of the Nervous System* 8(2):37-39-46.

Meduna, L.J. (Nov. 1948). "Alteration of Neurotic Pattern by Use of $CO_2$ Inhalations," in *The Journal of Nervous and Mental Disease, Special Number, Socity of Biological Psychiatry*, Washington, D.C, 108(5):373-379.

Meduna L.J. ed. (1958). "Carbon Dioxide Therapy a Neurophysiological Treatment of Nervous Disorders," 2nd Edition. Bannerstone House: Springfield, IL, pp. 1-541.

Mischler, S.A. et al. (1994). "Prolonged Antinociception Following Carbon Dioxide Anesthesia in the Laboratory Rat," *Brain Research* 640:322-327.

Moriarty, J.D. (Sep. 1952). "Carbon Dioxide Inhalation Therapy of Neuroses," *Journal of Clinical and Experimental Psychopathology* 13(3):181-194.

Moriarty, J.D. (1958). "Prognosis with Carbon Dioxide Therapy, Including the Epinephrine-Mecholyl Test (Funkenstein Test)," in *Carbon Dioxide Therapy a Neurophysiological Treatment of Nervous Disorders. 2nd Edition*, L.J. Meduna ed., Bannerstone House: Springfield, IL. pp. 376-395.

National Headache Foundation. (Aug. 1996). "A Patients Guide to Migraine Prevention & Treatment," 6 pages.

Navarra, P. et al. (1996). "Gaseous Neuromodulators in the Control of Neutroendocrine Stress Axis," *Ann. NY Acad. Sci.* 917:638-646.

Nielsen, T.M. et al. (1976). "The Effect of $CO_2$ on Peripheral Airways," *Acta Physiol. Scand.* 98:192-199.

Pagano, D. et al. (1996). "A Comparison o fInhaled Nitric Oxide with Intravenous Vasodilators in the Assessment of Pulmonary Haemodynamics Prior to Cardiac Transplantation," *Eur J Cardiothorac Sug* 10(12):1120-1126.

Qi, S. et al. (Jan. 1996). "An Experiment Study of Reversed Pulmonary Hypertension with Inhaled Nitric Oxide on Smoke Inhalation Injury," *Chin J. Surg.* 35(1):56-58. (Abstract Only).

Ream, R.S. et al. (1999). "Low-Dose Inhaled Nitric Oxide Improves the Oxygenation and Ventilation of Infants and Children with Acute, Hypoxemic Respiratory Failure," *Crit. Care Med.* 27(5): 989-996.

Rodarte, J.R. et al. (1973). "Effect of Acute Exposure to $CO_2$ on Lung Mechanics in Normal Man," *Respiration Physiology* 17:135-145.

Sand, G.H. (2002). "Oxygen Therapy for Headaches," located at <www.headaches.org/consumer/topicsheets/oxygen.html>, last visited Nov. 7, 2002, 2 pages.

Saqueton, C.B. et al. (Jun. 1999). "No Causes Perinatal Pulmonary Vasodilation through K+-Channel Activation and Introcellular Ca2+ Release," *Am. J. Physiol.* 276(6 Pt 1):L925-L932.

Schaeffer, E.M. et al. (1999). "Oxygenation in Status Asthmaticus Improves During Ventilation with Helium-Oxygen," *Crit Care Med* 27(12):2666-2670.

Schenk, P. et al. (Jun. 1999). "Inhaled Nitric Oxide in a Patient with Severe Pulmonary Embolism," *Annals of Emergency Medicine* 33(6):710-714.

Schuttauf, F. et al. (1998). "Influence of Various Mixtures of Breathing Gases on ocular Blood Flow Velocities Obtained by Color Doppler Imaging," *Opthalmologe* 95:225-228.

Serber, E. (Jan./Feb. 1999). "Yoga Cure for Headaches, When Neck Tension is at the Root of Your Headaches, Yoga Can Help Alleviate the Pain," located at <www.yogajournal.com/health/121.cfm>, last visited Nov. 7, 2002, 4 pages.

Serber, E. (May 2001). "Yoga: A Cure for Headaches," located at <www.shared-vision.com/old_site/01m05/storyc01.html>, last visited Nov. 7, 2002, 3 pages.

Silkoff, P.E. et al. (May/Jun. 1999). "Nasal Nitric Oxide: A Comparison of Measurement Techniques," *Am. J. Rhinol.* 13(3):169-178.

Singh, V. et al. (1990). "Effect of Yoga Breathing Exercises (Pranayama) on Airway Reactivity in Subjects with Asthma," *Lancet* 335:1381-1383.

Sterling, G.M. et al. (Jan. 1972). "Effect of $CO_2$ and pH on Bronchoconstriction Caused by Serotonin vs. Acetylcholine," *Journal of Applied Physiology* 22(1):39-43.

Tang, A. et al. (1972). "Effect of $CO_2$ on Serotonin-Induced Contraction of Isolated Smooth Muscle," *Clinical Research* pp. 243.

Telepchak, J.M. (Jan. 1997). "Smoking Cessation: New Strategies and Opportunities for Pharmacists," *American Druggist* 214(1):48-56.

Wilkinson, W.E. (1958). "Some Clinical Observations Pertaining to the Effects of Carbon Dioxide on the Biology of Mental Disease," in

*Carbon Dioxide Therapy a Neurophysiological Treatment of Nervous Disorders. 2nd Edition*, L.J. Meduna ed., Bannerstone House: Springfield, IL. pp. 165-201.

Wilmoth, D.F. et al. (Nov. 1996). "Preventing Complications of Mechanical Ventilation: Permissive Hypercapnia," *AACN Clin. Issues* 7(4):473-481.

Zysk, K.G. (1993). "The Science of Respiration and the Doctrine of the Bodily Winds in Ancient India," *Journal of American Oriental Society* 113(2):198-213.

Declaration by ned Rasor regarding use of invention prior to filing, Nov. 2003.

Final Office Action mailed on Jan. 25, 2010, for U.S. Appl. No. 11/456,477, filed Jul. 10, 2006, 7 pages.

Final Office Action mailed on Feb. 17, 2010, for U.S. Appl. No. 11/456,486, filed Jul. 10, 2006, 6 pages.

Non-Final Office Action mailed on Jun. 16, 2008, for U.S. Appl. No. 11/456,477, filed Jul. 10, 2006, 7 pages.

Non-Final Office Action mailed on Jun. 18, 2008, for U.S. Appl. No. 11/456,486, filed Jul. 10, 2006, 7 pages.

Non-Final Office Action mailed on Jun. 20, 2008, for U.S. Appl. No. 11/534,119, filed Sep. 21, 2006, 7 pages.

Non-Final Office Action mailed on Jun. 26, 2008, for U.S. Appl. No. 11/456,490, filed Jul. 10, 2006, 7 pages.

Non-Final Office Action mailed on Oct. 17, 2008, for U.S. Appl. No. 11/456,486, filed Jul. 10, 2006, 7 pages.

Non-Final Office Action mailed on Oct. 20, 2008, for U.S. Appl. No. 11/456,477, filed Jul. 10, 2006, 7 pages.

Non-Final Office Action mailed on Oct. 20, 2008, for U.S. Appl. No. 11/456,490, filed Jul. 10, 2006, 7 pages.

Non-Final Office Action mailed on Oct. 21, 2008, for U.S. Appl No. 11/534,119, filed Sep. 21, 2006, 8 pages.

Non-Final Office Action mailed on Jul. 16, 2009, for U.S. Appl. No. 11/534,119, filed Sep. 21, 2006, 7 pages.

Non-Final Office Action mailed on Jul. 17, 2009, for U.S. Appl. No. 11/456,477, filed Jul. 10, 2006, 6 pages.

Non-Final Office Action mailed on Jul. 17, 2009, for U.S. Appl. No. 11/456,486, filed Jul. 10, 2006, 5 pages.

Non-Final Office Action mailed on Jul. 17, 2009, for U.S. Appl. No. 11/456,490, filed Jul. 10, 2006, 7 pages.

Non-Final Office Action mailed on Mar. 22, 2010, for U.S. Appl. No. 11/456,490, filed Jul. 10, 2006, 6 pages.

Non-Final Office Action mailed on Mar. 23, 2010, for U.S. Appl. No. 11/534,119, filed Sep. 21, 2006, 6 pages.

Non-final Office Action mailed Apr. 14, 2011, for U.S. Appl. No. 12/708,407, filed Feb. 18, 2010, 6 pages.

Extended European search Report mailed on Oct. 30, 2007, for EP Application No. 06019590.6, filed Jul. 12, 2000, 9 pages.

International Search Report mailed Dec. 27, 2000, for PCT Patent Application No. PCT/US00/19043, filed Jul. 12, 2000, 5 pages.

International Search Report mailed Jun. 28, 2001, for PCT Patent Application No. PCT/US2001/40195, filed Feb. 28, 2001, 1 page.

International Search Report mailed Feb. 8, 2002, for PCT Patent Application No. PCT/US2000/41956, filed Nov. 7, 2000, 1 page.

International Preliminary Report on Patentability mailed Mar. 4, 2003, for PCT Patent Application No. PCT/US2000/41956, filed Nov. 7, 2000, 3 pages.

Non-Final Office Action mailed on Oct. 30, 2012, for U.S. Appl. No. 12/917,141, filed Nov. 1, 2010, 5 pages.

Notice of Allowance mailed on Sep. 19, 2012, for U.S. Appl. No. 12/917,141, filed Nov. 1, 2010, 5 pages.

* cited by examiner

METHODS AND APPARATUS FOR TREATING RHINITIS

This application is a continuation of U.S. patent application Ser. No. 11/459,798, filed Jul. 25, 2006; which is a continuation-in-part of U.S. patent application Ser. No. 11/192,852, filed Jul. 29, 2005; which is a continuation-in-part of U.S. patent application Ser. No. 09/708,186, filed Nov. 7, 2000 (now U.S. Pat. No. 6,959,708); which claimed the benefit of U.S. Provisional Patent Application Nos. 60/185,495, filed Feb. 28, 2000, and 60/164,125, filed Nov. 8, 1999. The contents of the above-identified applications are incorporated herein by reference in their entirety

BACKGROUND OF THE INVENTION

1. Field of the Invention

The present invention relates to drug delivery. More particularly, the present invention relates to methods and apparatus for delivering agents to mucosal and other tissue surfaces, in the presence of capnic gases, particularly for the treatment of rhinitis.

Drug delivery to mucosal surfaces, such as the mucosa of the nose, is well known. While in some cases drugs delivered to the nose and other mucosal surfaces are intended to have local effect, more often such transmucosal drug delivery is intended for systemic administration. In either case, penetration of the drug into or through the mucosa is limited by the ability of the particular drug to pass into or through the mucosal cell structure. Such resistance from the mucosal cell structure can result in slowing of the delivery, the need to use higher dosages of the drug, or in the case of larger molecules, the inability to deliver via a nasal or other mucosal route.

A walk through the cold and allergy section of any pharmacy quickly reveals that there is wide spread interest in remedies for relieving symptoms commonly associated with allergies, colds, asthma, and other common ailments which have symptoms of rhinitis e.g., runny noses and watery eyes. The commonly available therapies include oral medicines, nasal sprays, oral inhalers, nasal inhalers, eye drops, and nose drops, and probably other devices and approaches that have been developed over the years. Still more possible therapies are available from the pharmacy with a prescription from a patient's doctor (e.g., injectables, inhalables). Despite the very large number of therapies which are available, no one therapy meets all patient needs, and many of the therapies suffer from very significant shortcomings. For example, present day therapies are slow-acting, may have numerous adverse side effects (e.g., drowsiness, rebound congestion from decongestant overuse, dizziness, sedation, addiction, and numerous others), have low efficacy, and are contraindicated for a large portion of patients (e.g., those with hypertension, coronary artery disease, cerebrovascular disease, peptic ulcers, pregnancy, concurrent medications that would interact, children, elderly, and others). Suffice it to say that there is a continuing interest in providing improved methods and apparatus for treating such common symptoms and ailments.

Very recently, the use of carbon dioxide and other capnic gases alone and in combination with other gases has been proposed for the treatment of rhinitis and other conditions. The carbon dioxide is preferably delivered to nasal or other mucosa without inhalation. It is believed that the carbon dioxide may cause an intracellular acidosis which inhibits the release of calcitonin gene-related peptide (CGRP) and other neuropeptides which in turn reduces nasal symptoms of rhinitis. It has also been found that the onset of relief with carbon dioxide is usually much more rapid than that achieved with antihistamines, intranasal corticosteroids, leukotriene antagonists, and other drug therapies.

Despite the promise of conventional drug therapies and the newer delivery of capnic gases, neither therapy is effective in all individuals and neither therapy is entirely effective in relieving rhinitis and associated symptoms in all circumstances. It would thus be desirable to provide improved methods and systems for treating rhinitis. In particular, it would be desirable to provide treatments which are more effective, more rapid, more long-lasting, and/or which have other benefits when compared to the administration of either known rhinitis drugs or capnic gases alone.

2. Description of Background Art

Inhalation devices, systems and methods for delivering carbon dioxide and other gases and aerosols to patients, with and without co-delivery of a drug are described in U.S. Pat. Nos. 3,776,227; 3,513,843; 3,974,830; 4,137,914; 4,554,916; 5,262,180; 5,485,827; 5,570,683, 6,581,539; and 6,652,479. While some methods and devices provide for co-delivery of a drug and carbon dioxide or other gases, the purpose is usually not potentiation. For example, carbon dioxide may be used as a safe propellant, as shown in Wetterlin, U.S. Pat. No. 4,137,914. See also copending application Ser. Nos. 09/614,389, 10/666,947, and 10/666,562; the full disclosures of which are incorporated herein by reference.

Additional background art may be found in the following references: Guyton A C, Hall J E. *Textbook of Medical Physiology*. Ninth Ed., W.B. Saunders Co., Philadelphia, 1996; Tang A, Rayner M, Nadel J. "Effect of $CO_2$ on serotonin-induced contraction of isolated smooth muscle," *Clin Research* 20:243, 1972; Qi S, Yang Z, He B. "An experimental study of reversed pulmonary hypertension with inhaled nitric oxide on smoke inhalation injury," *Chung Hua Wai Ko Tsa Chih* 35(1):56-8, January 1997; Loh E, Lankford E B, Polidori D J, Doering-Lubit E B, Hanson C W, Acker M A. "Cardiovascular effects of inhaled nitric oxide in a canine model of cardiomyopathy," *Ann Thorac Surg* 67(5): 13 80-5, May 1999; Pagano D, Townend J N, Horton R, Smith C, Clutton-Brock T, Bonser R[S]. "A comparison of inhaled nitric oxide with intravenous vasodilators in the assessment of pulmonary haemodynamics prior to cardiac transplantation," *Eur J Cardiothorac Surg* 10(12):1120-6, 1996; and Sterling G, et al. "Effect of CO2 and pH on bronchoconstriction caused by serotonin vs. acetylcholine," *J of Appl Physiology*, vol. 22, 1972.

SUMMARY OF THE INVENTION

The present invention provides methods and apparatus for treating patients, particularly patients suffering or at risk of suffering from rhinitis, by administering a treatment agent to the patient and simultaneously delivering a capnic gas to a nasal, oral, auricular, or ocular membrane of the patient. By "simultaneously," it is meant that the treatment agent will be administered and the capnic gas delivered at the same time or within a very short time of each other, typically within 60 minutes, preferably within 30 minutes, and more preferably within 10 minutes. In some instances, it may be desirable to deliver the treatment agent together with the capnic gas, e.g., where the capnic gas can act as a carrier for the treatment agent. It will be more common to deliver the treatment agent separately in a separate dosage form, such as any of the dosage forms which are commonly available for the particular treatment agents described below. While the treatment agent will often be delivered systemically, in other cases it may be delivered orally to the target mucosa and have a local effect in the mucosal tissue.

In preferred protocols, at the onset of a rhinitis attack, the patient would take a dose of the treatment agent and substantially simultaneously initiate delivery of the capnic gas to the target membrane. The capnic gas would provide a rapid onset of action, possibly by inhibiting the release of CGRP as described above, in order to interrupt or delay progression of the rhinitis attack. At the same time, the treatment agent would begin to function by its particular mode of action. The patient would experience a more effective treatment in one of several ways. As the capnic gas would at least slow the progression of the rhinitis attack, the symptoms would be less intense by the time the treatment agent becomes effective. The magnitude of congestion, runny nose, watery eyes, and associated symptoms experienced by the patient should be lessened at all points during the treatment. In other cases, the patient might benefit by reducing the dosage of the treatment agent and thereby reducing side effects.

Rhinitis is the medical term describing irritation and inflammation principally of the nose. Symptoms include a runny nose, sneezing, congestion and irritation in the nose, eyes, throat and ears. Rhinitis is related to and often occurs together with other disorders such as asthma and sinusitis. It is chronic or acute inflammation of the mucous membrane of the nose due to viruses, bacteria or irritants. The inflammation results in excessive mucous production producing a runny nose, nasal congestion and postnasal drip.

Exemplary systemic treatment agents useful in the methods of the present invention include antihistamines; H1 receptor antagonists, such as fexofenadine, cetirizine, loratidine, desloratadine, and azelastine; corticosteroids, such as fluticasone, mometasone, budesonide, triamcinolone, and flunisolide; leukotriene receptor antagonists, such as montelukast; anticholinergics, such as ipratropium; mast cell stabilizers, such as cromolyn; decongestants, such as oxymetazoline, pseudoephedrine and other alpha-adrenergic agonists.

The treatment agents may be delivered in any conventional form, including oral dosage forms (tablets, gels, capsules, and the like), intranasal forms (in which case they could optionally be combined with delivery of the capnic gases), forms intended for pulmonary delivery, injectable forms, and topical forms (for transcutaneous delivery).

Preferred capnic treatment gases include carbon dioxide, nitric oxide, nitrous oxide, and dilute acid gases, such as dilute hydrochloric acid and the like. Particularly preferred are carbon dioxide gases having a relatively high concentration, typically greater than 10% by volume, usually greater than 20% by volume, and preferably greater than 25% by volume and often being as great as 80% by volume, 90% by volume, and in many instances being substantially pure. The capnic gases may be used in combinations of one or more adjuvant gases and/or may be combined with physiologically inert gases such as nitrogen, to control concentration of the capnic gases.

The capnic gas is delivered to a nasal, oral, auricular, or ocular membrane of the patient, typically using a hand-held or other dispenser. Preferably, the capnic gas will be delivered to a nasal or oral mucosa, while the patient refrains from inhaling the capnic gas. In the exemplary embodiments, the capnic gas is infused through a nostril and exits through a nostril and/or the mouth. The patient will refrain from inhaling, typically by holding the velum in the throat closed, while the capnic gas is infused. In other instances, the capnic gas will be infused through the mouth and be allowed to exit through at least one nostril, usually both nostrils. In those instances, the patient will also refrain from inhaling the gas.

The capnic gases will usually be delivered using a dispenser. Typically, the dispenser includes a pressurized source of the capnic gas and a valve assembly for releasing the gas at a controlled flow rate, typically in the range from 0.5 cc/sec to 30 cc/sec in the case of high concentration of carbon dioxide. Optionally, the treatment agent may be dissolved or suspended in the pressurized capnic gas for simultaneous delivery. Alternatively, the treatment agent may be delivered simultaneously from a separate receptacle, either through the same or a different delivery path. Often, the capnic gas and the treatment agent, even when stored in separate receptacles, will be delivered through a common conduit and nozzle to allow for both simultaneous and sequential delivery.

DETAILED DESCRIPTION OF THE INVENTION

Figure 1:
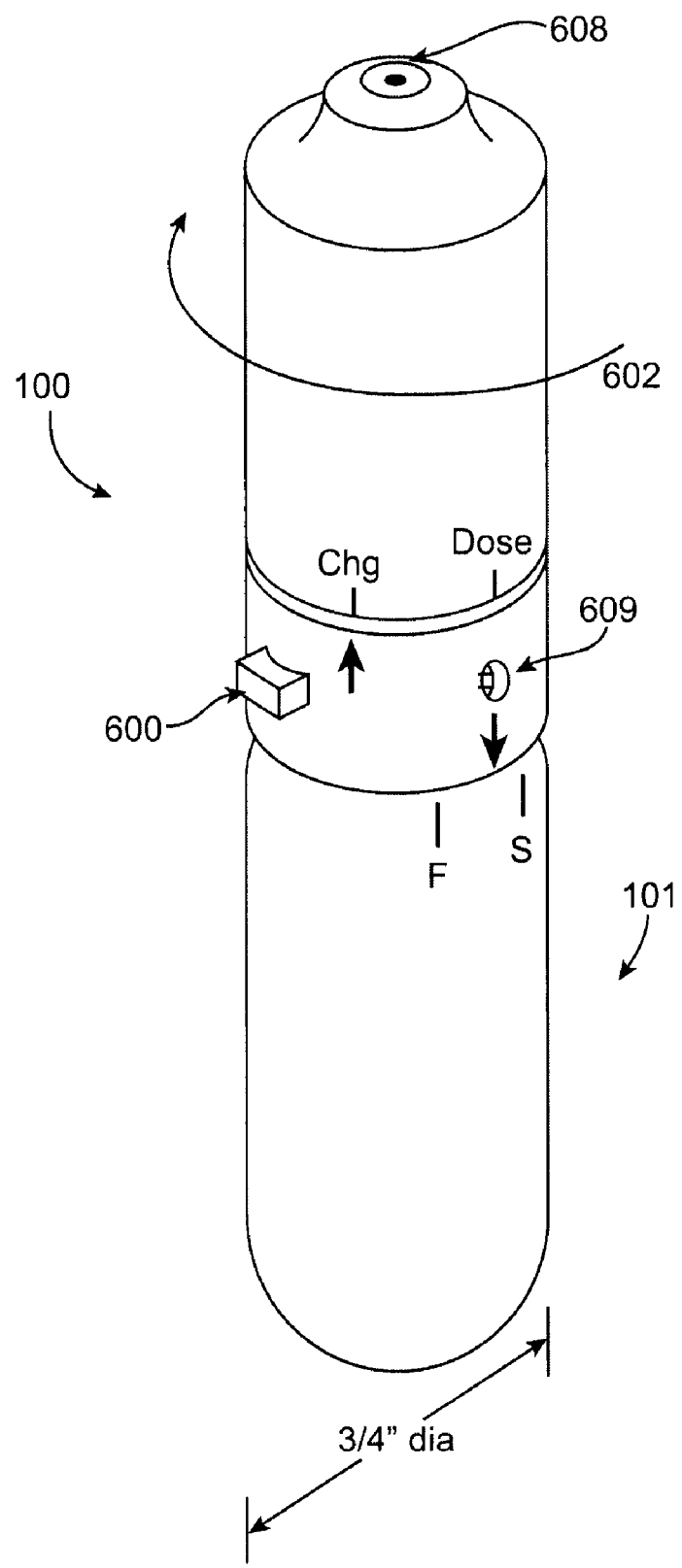
FIG. 1 illustrates an exemplary capnic gas infusion device, illustrating a charge/dose and dose rate adjustment features.

An exemplary carbon dioxide dispenser 100 comprising a carbon dioxide cartridge 101 is illustrated in FIG. 1. The embodiment of FIG. 1 is described in greater detail in parent application Ser. No. 09/708,186, now U.S. Pat. No. 6,959,708, the full disclosure of which has previously been incorporated herein by reference. A user delivers a dose of carbon dioxide or other treatment agent, referred to generally as "capnic gases" (optionally carrying the systemic treatment agent to be delivered) by applying the top of the dispenser 608 to the user's nose or mouth and pushing a button 600 which releases an internal mechanism to allow the $CO_2$ to flow from the top of the dispenser 608. The internal mechanism will lower the pressure of $CO_2$ in the cartridge and will control the flow rate within suitable ranges, typically from 0.5 to 30 cc/sec. The flow rate may be maintained for a suitable time period, typically at least 2 seconds when suffusing the nasal and sinus passages. The device is cocked by rotation as shown by arrow 602 and pushing the button 600 to deliver the dose by an automatic counter-rotation. The user may select the specific carbon dioxide flow rate by setting at a set screw through aperture 609.

The dispenser 100 of FIG. 1 may be used to deliver any of the capnic gases in accordance with the principles of the present invention. The capnic gases may be delivered with or without the systemic treatment agent incorporated in the canister 101. In cases where the capnic gas is to be delivered by itself, at some suitable concentration, the systemic treatment agent will have to be delivered systemically in some other manner. The systemic treatment agent could be delivered in any of the conventional dosage forms described above or could be delivered to the target mucosa by suffusion or infusion, by placing a liquid, powder, or the like over the tissue surface, by introducing a vapor, mist, or the like using conventional drug delivery vapor sources and misters, or the like.

Figure 2:
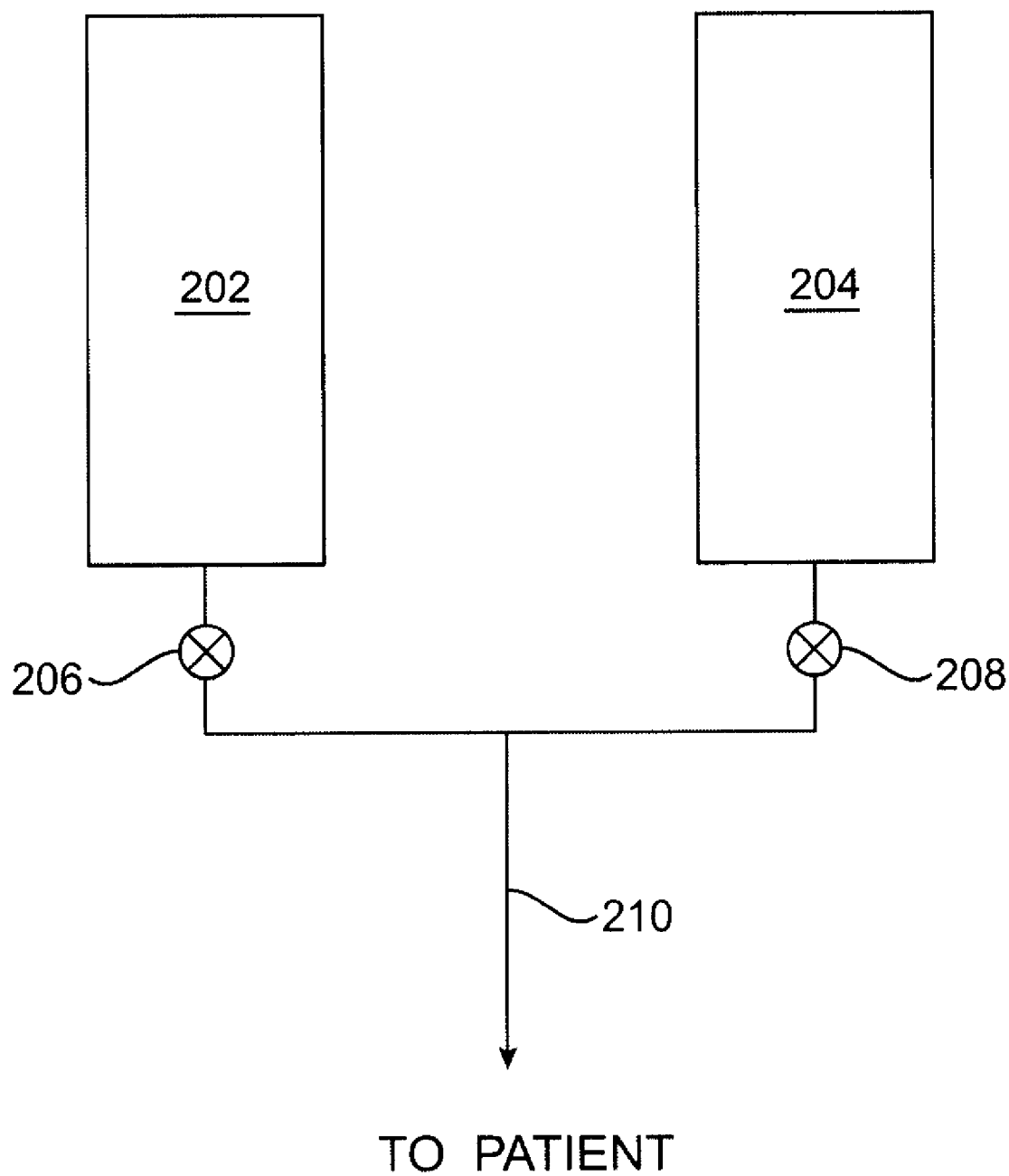
FIG. 2 is a schematic illustration of a delivery system incorporating separate receptacles for the capnic and the treatment agent, where the receptacles are joined through valves into a common delivery conduit.

FIG. 2 is a schematic illustration showing a system for simultaneous or closely separated sequential delivery of the capnic gas and systemic treatment agent. The capnic gas is held in a separate cartridge or other container 202 while the systemic treatment agent is held in a cartridge or other container 204. Both the gas and the systemic treatment agent will be in a gaseous, vapor, mist, or other flowable form which permits them to pass through associated valves 206 and 208 respectively, and thereafter through a conduit 210 which receives flow from both valves. The valves will be suitable for controlling both flow rate and pressure of the capnic gas and the systemic treatment agent. It will be appreciated that more complex delivery systems can be provided including flow rate measurement, feedback control, temperature control, timers, and the like.

Figure 3A:
FIGS. 3A-3E show application of the capnic gas optionally in combination with the treatment agent to the nose, mouth, both nostrils, eye, and ear, using a gas dispenser according to the present invention.
Figure 3B:
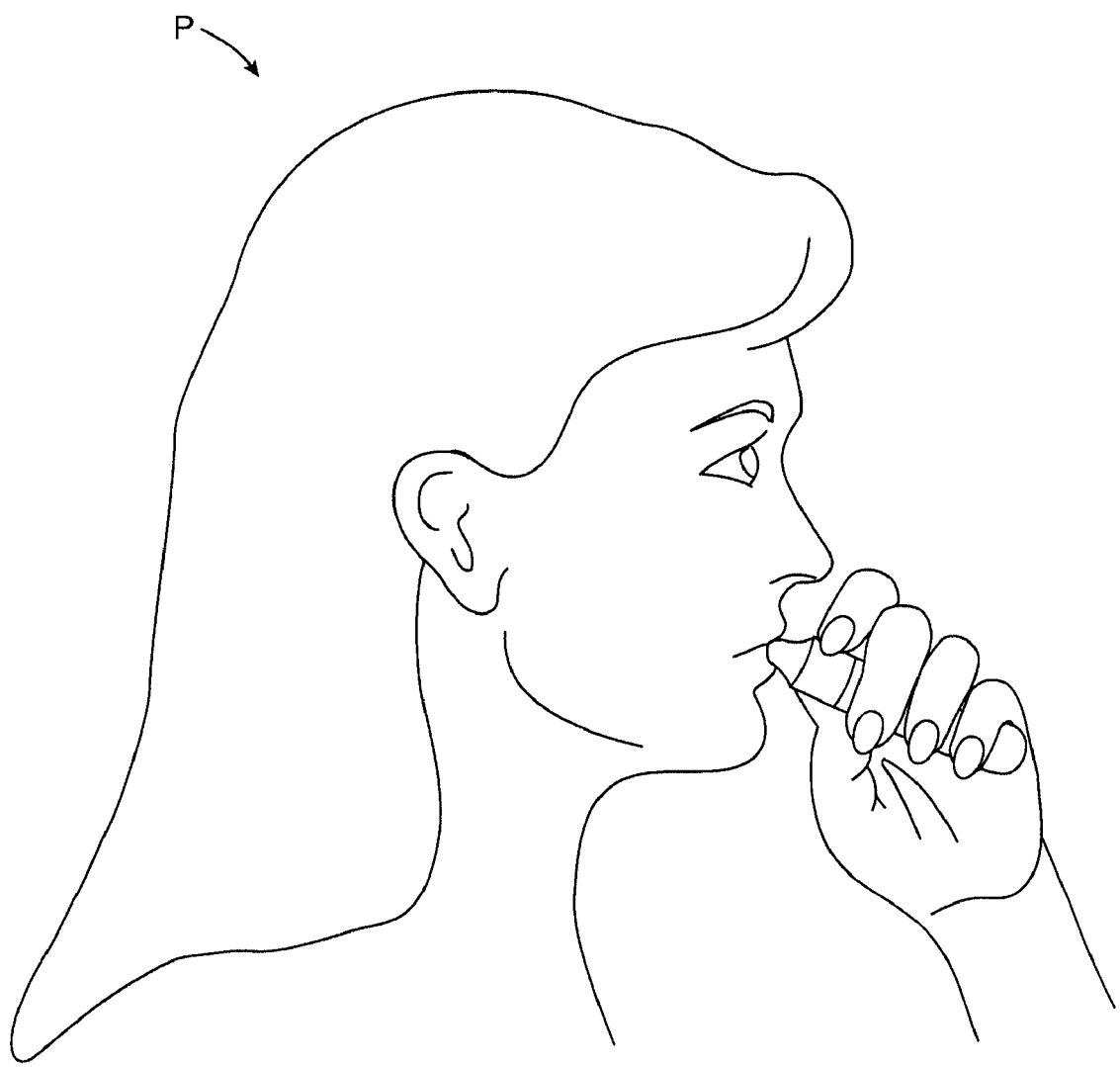
Figure 3C:
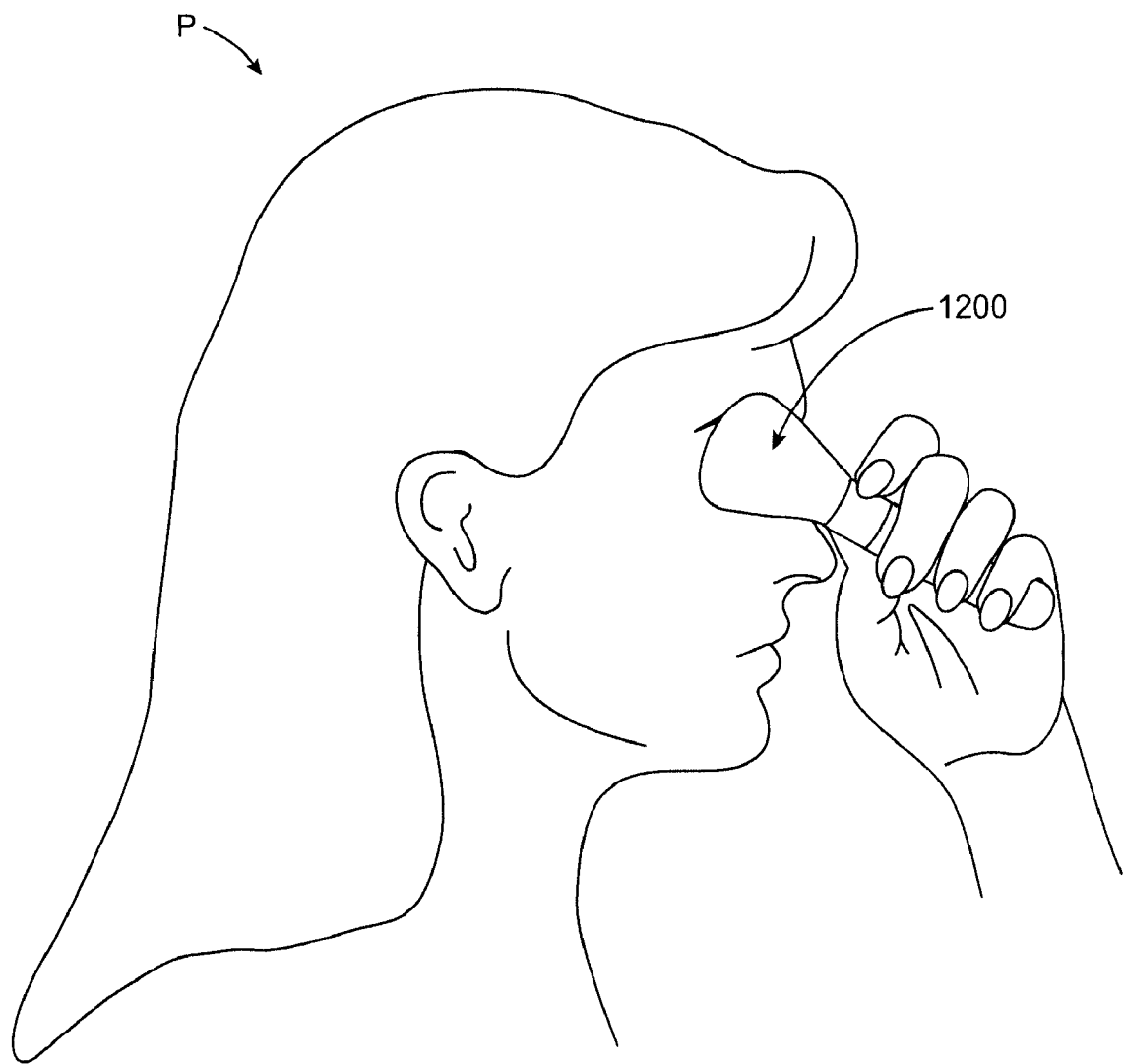
Figure 3D:
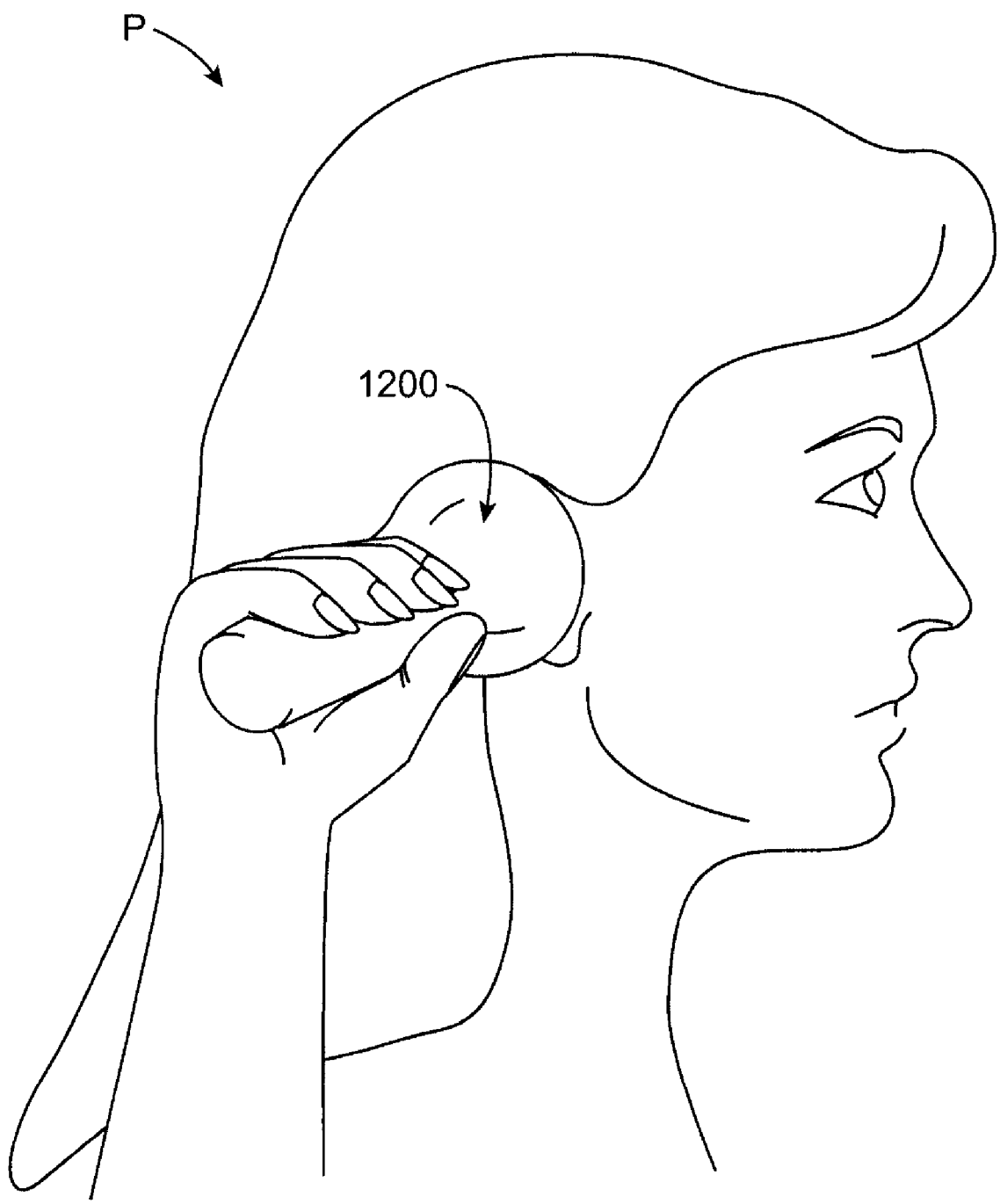
Figure 3E:
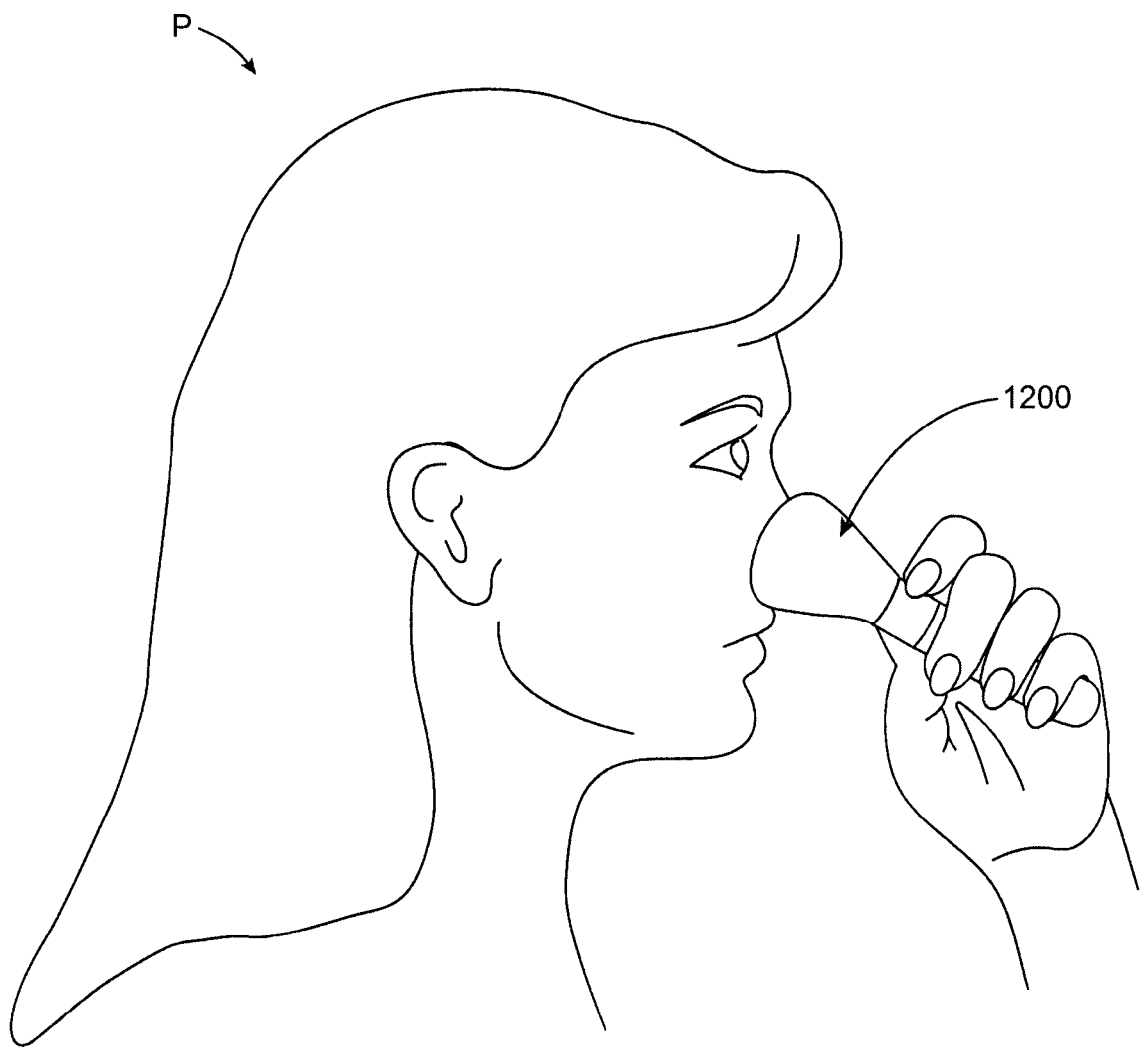

Referring now to FIGS. 3A to 3E, a variety of ways for effecting mucosal infusion with the capnic gas, optionally combined with the systemic treatment agent, are illustrated. The capnic gas is preferably infused at a flow rate in a range from 0.5 cc/sec to 30 cc/sec, depending on the tolerance of the individual being treated. In some instances, the selected drug or other systemic treatment agent can be delivered separately by suffusion, infusion, misting, the application of powder, or the like. As shown in FIG. 3A-B, the individual P infuses oral and nasal mucous membranes by placing the source of low flow rate $CO_2$ (or other mixed gas) or other appropriately physiologically active gas or vapor in or around a facial orifice, such as the mouth or nostril, while substantially inhibiting the flow of the $CO_2$ into the trachea and lungs by limiting inhalation of the $CO_2$. If the mouth is infused the gas is allowed to exit from the nostrils. Alternatively, one or both nostrils may be infused either by using the dispenser head shown in FIG. 3B or by use of a cup or similar device that covers both nostrils as shown in FIG. 3E. The gas is allowed to flow from a remaining open orifice, i.e., either the mouth, the uninfused nostril, or both as appropriate. Completely holding the breath is not necessary to substantially prevent inhalation of the $CO_2$. With practice, it is possible for the individual to breathe through an uninfused orifice. For example, if one nostril is infused and the gas is allowed to exit though the other nostril, it is possible for the individual to breathe through the mouth without substantial inhalation of the infused gas. The eye or eyes may also be infused using a cup as shown in FIG. 3C or merely by holding a hand over the eye and releasing the gas between the hand and the eye. Persons of ordinary skill in the art will appreciate that a double cup could be developed to infuse both eyes simultaneously, and similarly appropriate heads could be developed to infuse the mouth and one nostril. The ear or ears may also be infused as shown in FIG. 3D. Note that a similar process may be used with the first embodiment to infuse a mixture of a drug and gas into various facial orifices.

Infusion can be continued to the limit of tolerance or until the desired potentiation effect is realized. Since most individuals develop a temporary increased tolerance after extended applications or repeated applications, it may be possible and desirable to increase the duration of additional infusions after a few applications when all applications occur within a short time of each other, i.e., approximately 1 to 20 minutes between each application.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating rhinitis, comprising:
   identifying a patient suffering from rhinitis;
   administering a treatment agent selected to treat rhinitis to the patient; and
   delivering a capnic gas to a nasal or oral membrane of the patient;
   wherein the treatment agent is selected from the group consisting of antihistamines, H1 receptor antagonist, corticosteroids, leukotriene receptor antagonists, mast cell stabilizers, anticholinergic agents, and decongestants; and
   wherein the treatment agent and capnic gas are administered and delivered simultaneously at a controlled flow rate in the range from 0.5 cc/sec to 30 cc/sec, and wherein the patient refrains from inhaling the capnic gas when the capnic gas is delivered to the nasal or oral membrane.

2. The method according to claim 1, wherein the treatment agent comprises an antihistamine.

3. The method according to claim 1, wherein the treatment agent comprises an H1 receptor antagonist selected from the group consisting of fexofenadine, cetirizine, loratidine, desloratadine, and azelastine.

4. The method according to claim 1, wherein the treatment agent comprises a corticosteroid selected from the group consisting of fluticasone, mometasone, budesonide, triamcinolone, and flunisolide.

5. The method according to claim 1, wherein the treatment agent comprises a leukotriene receptor antagonist.

6. The method according to claim 1, wherein the treatment agent comprises an anticholinergic agent.

7. The method according to claim 1, wherein the treatment agent comprises a mast cell stabilizer.

8. The method according to claim 1, wherein the treatment agent comprises a decongestant selected from the group consisting of oxymetazoline and pseudoephedrine.

9. The method according to claim 1, wherein the treatment agent comprises an alpha-adrenergic agonist.

10. The method according to claim 1, wherein the capnic gas delivered to the nasal membrane is infused through a nostril and exits through a nostril and/or the mouth.

11. The method according to claim 1, wherein the capnic gas delivered to the oral membrane is infused through the mouth and exits through at least one nostril and/or the mouth.

12. The method according to claim 1, wherein the capnic gas comprises carbon dioxide at a concentration of at least 50% by volume.

13. The method according to claim 1, wherein the capnic gas is selected from the group consisting of carbon dioxide, nitric oxide, nitrous oxide, and dilute acid gases.

14. The method according to claim 13, wherein the capnic gas comprises carbon dioxide.

15. The method according to claim 14, wherein the carbon dioxide is present at a concentration of at least 50% by volume.

16. The method according to claim 15, wherein the carbon dioxide is substantially pure.

17. A method for treating rhinitis, comprising:
   identifying a patient suffering from rhinitis;
   administering a treatment agent selected to treat rhinitis to the patient; and
   delivering a capnic gas to a nasal or oral membrane of the patient;
   wherein the treatment agent is selected from the group consisting of antihistamines, H1 receptor antagonist, corticosteroids, leukotriene receptor antagonists, mast cell stabilizers, anticholinergic agents, and decongestants; and
   wherein the treatment agent and the capnic gas are administered and delivered within sixty minutes of each other at a controlled flow rate in the range from 0.5 cc/sec to 30 cc/sec, and wherein the patient refrains from inhaling the capnic gas when the capnic gas is delivered to the nasal or oral membrane.

* * * * *